United States Patent [19]

D'Errico

[11] 4,044,403
[45] Aug. 30, 1977

[54] IMPLANTABLE JOINT PROSTHESIS

[75] Inventor: Joseph D'Errico, Clifton, N.J.

[73] Assignee: Howmedica, Inc., New York, N.Y.

[21] Appl. No.: 737,586

[22] Filed: Nov. 1, 1976

[51] Int. Cl.² .................................................. A61F 1/24
[52] U.S. Cl. ........................................ 3/1.913; 3/1.91;
128/92 C; 128/92 CA
[58] Field of Search ........................... 3/1, 1.91–1.913;
128/92 C, 92 CA

[56] References Cited

U.S. PATENT DOCUMENTS

| | | | |
|---|---|---|---|
| 3,813,699 | 6/1974 | Giliberty | 3/1.912 |
| 3,818,512 | 6/1974 | Shersher | 3/1.912 |
| 3,842,442 | 10/1974 | Kolbel | 3/1.91 |
| 3,863,273 | 2/1975 | Averill | 3/1.91 |
| 3,916,451 | 11/1975 | Buechel et al. | 3/1.91 |
| 3,922,726 | 12/1975 | Trentani et al. | 3/1.912 |
| 3,965,490 | 6/1976 | Murray et al. | 3/1.913 |
| 3,978,528 | 9/1976 | Crep | 3/1.91 |
| 3,982,281 | 9/1976 | Giliberty | 3/1.913 |

Primary Examiner—Ronald L. Frinks
Attorney, Agent, or Firm—Pennie & Edmonds

[57] ABSTRACT

An articulating joint prosthesis comprising implantable first and second members, said first member having a substantially spherical head, said second member having substantially congruent cavity formed therein for cooperatively engaging said spherical head, said cavity having a hemispherical portion terminating in a diametral plane and an entrance portion extending beyond said plane and terminating in a circular entrance to said cavity, an outwardly tapering guideway surrounding said entrance, said second member further having a continuous annular groove formed substantially at said diametral plane and adjacent said guideway, said guideway and said groove defining between them a resilient annular lip surrounding said entrance, said lip being inwardly deformable during insertion of said spherical head through said entrance to admit and entrap said head in said cavity, and said lip being outwardly deformable to resist escape of said head from said cavity.

9 Claims, 8 Drawing Figures

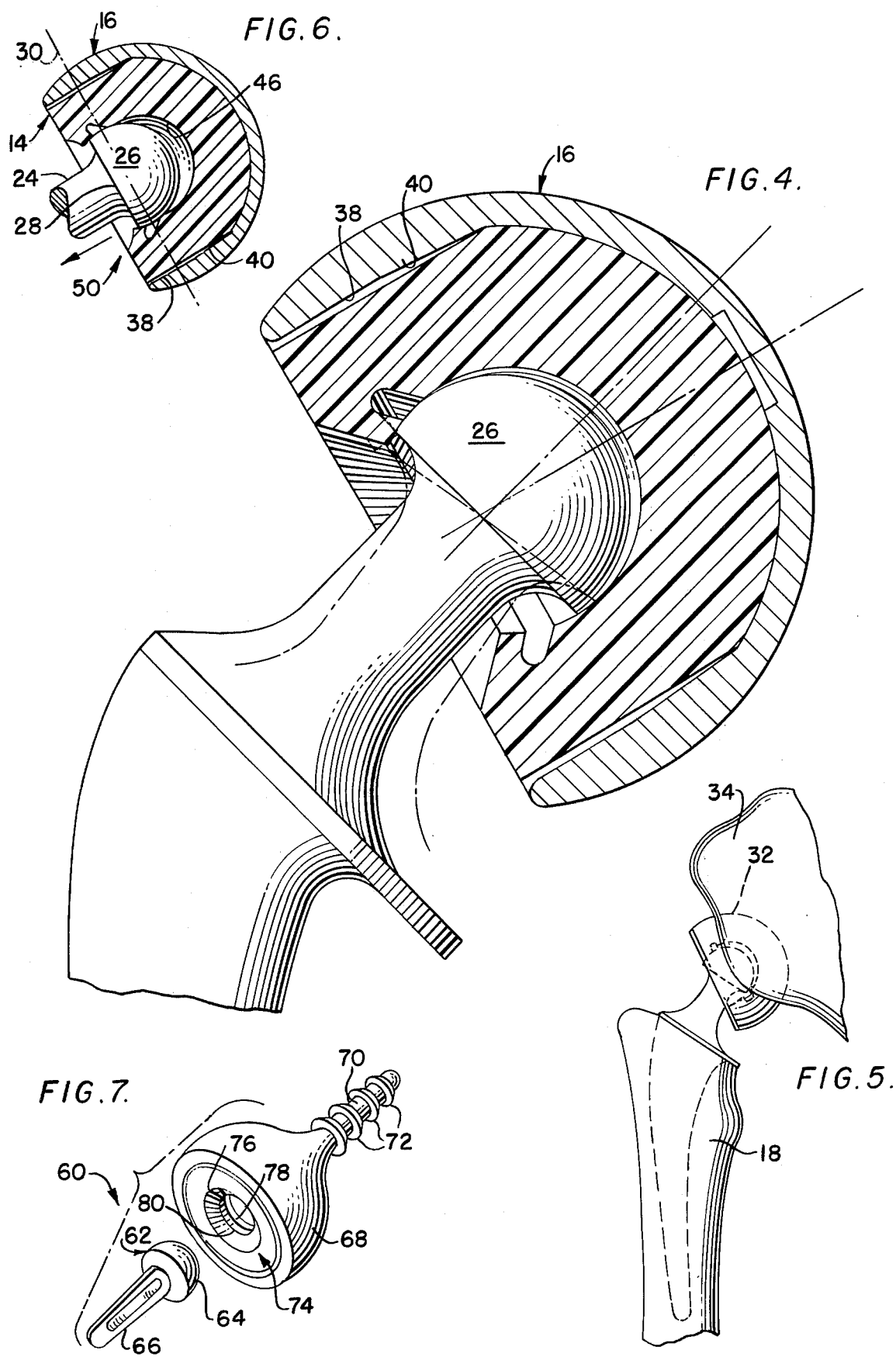

IMPLANTABLE JOINT PROSTHESIS

BACKGROUND OF THE INVENTION

1. Field of the Invention

This invention relates to implantable artificial devices for application in the human body. More particularly it is directed to a prosthetic device which substitutes for articulating anatomical joints.

2. Description of the Prior Art

The utilization of artificial devices which are implantable in the human body for replacing defective, damaged or diseased anatomical structure has long been known. One known specific form of prior art prosthetic device is for use in replacing anatomical joints of the body having ball and socket characteristics, as, for example, the hip joint. Such type of prosthesis essentially provides a detachable interconnection between the femur and acetabulum socket of the pelvis which serves the purpose of accomplishing the universal type movement associated with the replaced natural biological joint. Convention prosthetic total hip joints normally embody an acetabulum type cup member having a spherical cavity which may be suitably secured in a variety of ways to the acetabulum socket of the pelvis, and an artifical femoral insert which is appropriately attached to the femur. The femur insert includes a smooth and substantially spherical head member which mates with and is rotatably supported by the spherical cavity of the cup member. As a result of this structural interrelationship a ball and socket type joint is created which permits the ordinary type of articulated motion associated with the human hip joint.

In this particular field there are several known approaches which provide for artificial articulated joints. By way of specific examples, reference is made to U.S. Pat. Nos. 3,813,699 and 8,863,273, primarily directed to implantable hip joint prostheses. The artificial hip joint generally described in the latter patent has a complicated construction. More specifically it requires the use of head and bearing insert members having rather precisely formed slots, grooves and projections which serve to cooperate with each other to form an assembled joint. Furthermore, the metallic outer shell of these devices is a necessary part of the assembly since one of its functions is to prevent the escape of the ball from the socket through deformation of the bearing insert. It will be appreciated that relatively significant manufacturing and cost factors tend to make the foregoing construction undesirable. The prostheses of both cited patents lack any provision whereby the artificial spherical femur head member is more tightly entrapped in the spherical cavity of the insert cup whenever the prosthesis is subject to forces which have a tendency to separate the femur head and the insert cup. Consequently, such types of prostheses are subject to joint dislocation. Additionally, neither of the described hip joint prostheses provides means which enable the insertion force associated with injecting the artificial femur head into the spherical cavity to be of a lesser magnitude than the force necessary to withdraw the femur head from the cavity.

Heretofore known prosthetic hip joint devices are characterized by relatively complicated structural arrangements which not only fail to effectively provide for a quick and easy insertion of the artificial femur head in the corresponding cavity of a cup member, but also fail to provide means which even more tightly entraps the femur head within the cavity in response to separation forces which would tend to dislocate or separate the femur head from the cavity.

SUMMARY OF THE INVENTION

It is an object of the present invention to provide an improved prosthesis characterized by an extremely easy and guided assembly of the component members, together with effective and positive entrapment of such members in the assembled condition, whereby a firm non-dislocatable prosthesis joint results.

The prosthesis of the present invention is an articulating joint comprising implantable first and second members, said first member having a substantially spherical head, said second member having a substantially congruent cavity formed therein for cooperatively engaging said spherical head, said cavity having a hemispherical portion terminating in a diametral plane and an entrance portion extending beyond said plane and terminating in a circular entrance to said cavity, an outwardly tapering guideway surrounding said entrance, said second member further having a continuous annular groove formed substantially at said diametral plane and adjacent said guideway, said guideway and said groove defining between them a resilient annular lip surrounding said entrance, said lip being inwardly deformable during insertion of said spherical head through said entrance to admit and entrap said head in said cavity, and said lip being outwardly deformable to resist escape of said head from said cavity.

A preferred embodiment of the instant invention is a hip joint prosthesis wherein said first member is provided with means for implanting in the femur and said second member has a substantially spherical outer surface for implanting in the acetabulum.

An especially preferred embodiment of the hip joint prosthesis just mentioned is one in which said second member is formed from a resilient low friction polymer encased in a metallic outer shell.

A particularly satisfactory form of the above hip prothesis is one in which said polymer is ultra high molecular weight polyethylene and said metallic shell has a generally smooth unbroken and spherical conformation.

This invention further contemplates an implantable component for cooperatively engaging an implantable prosthetic member having a substantially spherical head to form an articulating joint prosthesis, said component having a substantially congruent cavity formed therein for cooperatively engaging said spherical head, said cavity having a hemispherical portion terminating in a diametral plane and an entrance portion extending beyond said plane and terminating in a circular entrance to said cavity, an outwardly tapering guideway surrounding said entrance, said second member further having a continuous groove formed substantially at said diametral plane and adjacent said guideway, said guideway and said groove defining between them a resilient annular lip surrounding said entrance, said lip being inwardly deformable during insertion of said spherical head through said entrance to admit and entrap said head in said cavity, and said lip being outwardly deformable to resist escape of said head from said cavity.

This implantable component is especially preferred when the walls of said annular groove are substantially parallel to the walls of said tapered guideway.

The implantable component is preferably constructed from a resilient low friction polymer. An especially preferred embodiment of this implantable component is one wherein said polymer is ultra high molecular weight polyethylene and said component is encased in a metallic outer shell which has a generally smooth unbroken and spherical conformation.

BRIEF DESCRIPTION OF THE DRAWING

The above and other objects, features and advantages of the present invention will be apparent from the appended detailed description of an embodiment thereof in conjunction with the accompanying drawing wherein like reference numerals indicate like structure throughout the several views.

FIG. 4 is an enlarged fragmented view, partly in section, illustrating the cooperating connection between the assembled components;

FIG. 5 is a schematic view illustrating a hip joint prosthesis applied to the human body;

FIG. 6 is a view illustrating the components of the instant invention when subjected to separating forces; and FIG. 7 is an exploded perspective view of a shoulder joint prosthesis.

DETAILED DESCRIPTION

Figure 1:
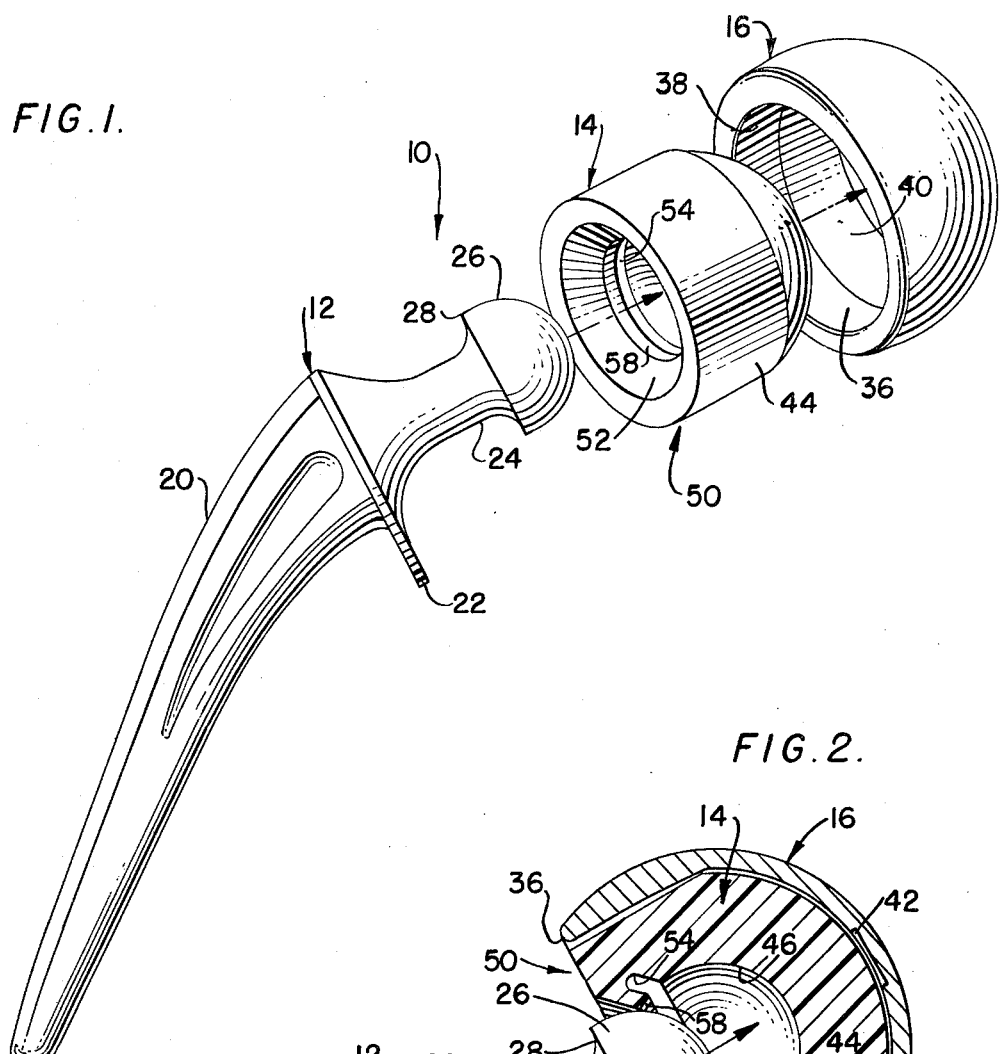
FIG. 1 is an exploded perspective view illustrating a hip joint prosthesis embodying the principles of the present invention.

FIG. 1 depicts an implantable hip joint prosthesis embodying the principles of this invention and designated generally by reference numeral 10. Although the succeeding description is primarily directed to a hip joint prosthesis, it should be emphasized that the spirit and scope of this invention envisions its application in other articulating anatomical joints. Moreover, the principles of this invention contemplate its application in human and veterinary uses. Thus, the following description of hip joint prosthesis 10 is for purposes of illustrating and should not be construed as a limitation of the present invention.

Figure 2:
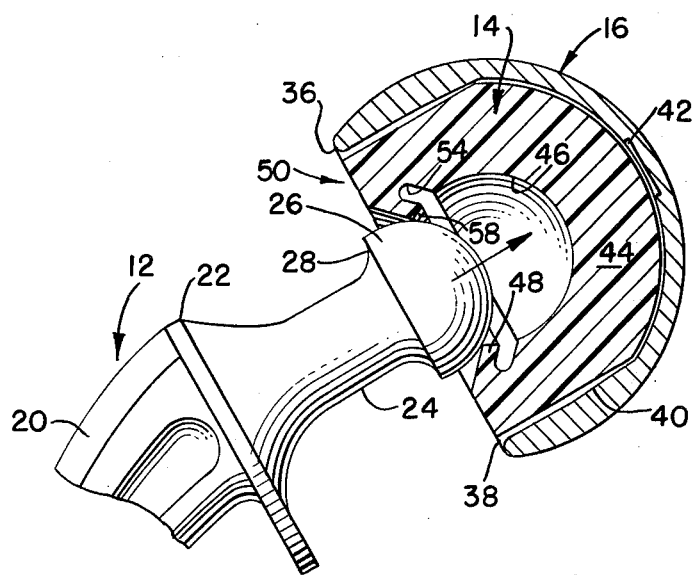
FIG. 2 is a fragmented view, partly in section, clearly demonstrating in greater detail components forming the anatomical hip joint prosthesis.

As depicted in FIG. 1 and FIG. 2, the hip joint prosthesis 10 includes an implantable first member, in this case artificial femur insert member 12, an implantable second member, (prosthesis means 14) and unitary acetabulum shield member 16 encasing said second member. In the assembled condition shown in FIGS. 4, 5, and 6, these components constitute an artificial articulatable anatomical joint which is adapted to be implantable in a human body for purposes of replacing diseased, defective or damaged hip joints, and providing for substantially the same type of articulated movement which would be normally associated with the natural biological hip joint.

Artificial femur insert member 12 may be a suitable and conventional prosthetic device adapted to be implanted in the femur 18 through well-known medical procedures. When inserted into the femur 18, the insert member 12 is intended to generally assume the position depicted in FIG. 5. Femur insert member 12 comprises, in integral combination, shank portion 20, shoulder portion 22, neck portion 24, and head member 26. Shank portion 20 may be defined by a generally elongated member which is insertable within the femur 18. Shoulder portion 22 is formed intermediate the insert femur 12 and suitably configured to have an enlarged area which properly positions it relative to the top of the femur 18. The natural femur head, which may have been diseased, defective or damaged, will have been removed prior to the insertion of the femur insert member 12. The neck portion 24 has a smooth exterior surface and a reduced diameter in relation to the shoulder portion 22. Such neck portion 24 interconnects shoulder portion 22 with head member 26. Head member 26 comprises a generally spherical configuration with a continuously smooth and highly polished external surface having low-friction characteristics. By virtue of such low-friction characteristics, there is facilitated an interfitting and cooperating relationship with prosthesis means 14 which facilitates a smooth and continuous type of relative movement between the two members. The spherical head member 26 terminates at a rearward edge 28 suitably spaced from the diametral plane which extends into the drawing along the diametral line 30. The significance attached to this relationship will be described later. Implantable femoral insert member 12 is made of a conventional material suitable for implantation in body tissue including the anatomical bone structure. An example of such a material is Vitallium®, the trademark of Howmedica Inc. for a cobalt-chromium alloy developed and used for cast partial and full dentures and for internal applications by surgeons. Vitallium is characterized by a specific gravity of 8.29; tensile strength, 95,000 lb./sq.in.minimum; 2% offset yield strength, 65,000 lb./sq.in.minimum; reduction of area, 8% minimum; elongation, 8% minimum, and modulus of elasticity, 30,000,000–32,000,000 lb./sq.in. When polished, it is exceedingly smooth and permanently lustrous. Its outstanding qualities are clinical inertness in relation to living tissues and high degree of resistance to corrosion.

An outer shell, acetabulum shield member, 16 is designed to securely receive and encase the prosthesis means 14 in this particular embodiment and to be placed within the acetabulum socket 32 formed in the pelvis 34 and arranged to receive the natural femur head. In the usual implantation procedure, such socket 32 is appropriately worked upon, in conventional medical or surgical fashion, so that it is able to accommodate the acetabulum shield member 16. There are several known expedients, such as cementing, whereby the shield member 16 may be secured if desired in the acetabulum socket 32. Usually, however, the shield member 16 is left unsecured and allowed to move freely within the acetabulum socket 32.

Referring to FIGS. 1 and 4, the shield member 16 may be defined as a shell of substantially spherical configuration having a continuously smooth exterior surface which is adapted to be placed within the acetabulum socket. If free articulation within the acetabulum socket is desired the exterior surface of shield member 16 should be highly polished. Likewise, the interior surface of the shield member 16 may be similarly continuously smooth or, if desired, can be provided with means to secure the shield member 16 to prosthesis means 14. Such interior surface is arranged so as to include a generally cylindrical portion 36 adjacent an open mouth end 38 of the shield member 16 and a progressively increasingly tapered section 40 situated inwardly of and merging with the cylindrical portion 36. In addition, the wall shield member may be provided with a central cylindrical depression 42. Prosthesis means 14 is appropriately engaged and secured within the acetabulum shield member 16. Shield member 16 may be fabricated from a material which possesses low-friction characteristics, sufficient strength to remain durable during repeated loadings, and compatibility with body tissue. One such known material is Vitallium®. Other suitable materials are, of course, envisioned so long as they possess the properties and characteristics indicated above.

Prosthesis means 14 is formed as an integral cup shaped structure. Prosthesis means 14 is inserted in and tightly housed by acetabulum shield member 16. The prosthesis means 14 is in intimate relationship with spherical head member 26 and is capable of producing an artificial articulatable joint, able to simulate the universal movement normally associated with the replaced biological joint.

Prosthesis means 14 is fabricated from a suitable resilient material which is compatible for implantation in the human body. Additionally, the material should possess good strength, low-friction and high lubricity properties. Since the prosthesis means 14 supports the spherical head member 26 for universal movement during an extended period of time, the foregoing properties are clearly desirable. In the present embodiment, Ultra High Molecular Weight Polyethylene (U.H.M.W.P.) provides an extremely satisfactory material which permits low friction movement of the spherical head 26 relative to prosthesis means 14. Although U.H.M.W.P. has been found to be very successful, other materials having similar properties may be employed without departing from the spirit and scope of this invention.

Referring specifically to FIG. 4, the prosthesis member 14 receives the spherical head member 26 in a centrally formed and substantially congruent cavity 46. Cavity 46 has smooth walls and an opening 48 which defines an entrance thereto for insertion and retention of head member 26. Spherical cavity 46 is appropriately dimensioned to snugly receive and support the head member 26 for universal movement. Entrance opening 48 is appropriately spaced from the diametral line 30, which results in the opening 48 being smaller than the diameter of cavity 46 and smaller than that of the head member 26. Correspondingly, the opening 48 restricts or inhibits the free movement of the head member 26 therethrough. This arrangement serves to appropriately retain the femur member head 26 within the cavity 46 and prevents disengagement or dislocation of such members in a positive and simple fashion.

Prosthesis means 14 is formed with lip means 50. Lip means 50 includes a generally smooth and tapered guideway or guide wall portion 52 which has its smaller diametered end terminate at opening 48. Such tapered guideway 52 provides clearance for the neck portion to allow the desired range of relative movement between head member 26 and prosthesis means 14 which is necessary to simulate the normal universal movement which occurs between the natural femur and acetabulum socket. Guideway 52 greatly facilitates inserting head member 26 into cavity 46. This is of significance in those situations in which it is necessary to reinsert the head member 26 into the prosthesis means 14 during a subsequent surgical operation.

Novel and improved lip means 50 further includes a substantially continuous annular groove 54 appropriately formed in the cavity 46, substantially at said diametral plane and adjacent said guideway. Groove 54 is generally concentric with the spherical cavity and generally parallel to the guideway 52. This orientation of said groove and said guideway defines there between a deformable lip member 56 having a free end surface 58. In the lip's undeformed condition, its free end surface 58 is contiguous with the spherical curvature defined by the internal cavity 46 and defines the opening 48 with a first diameter. As earlier noted, the opening 48 restricts the free passage of head member 26. Since prosthesis means 14 is made of a material which is sufficiently flexible, lip member 56 deforms during the insertion procedure, as shown in FIGS. 2 through 4.

Figure 2A:
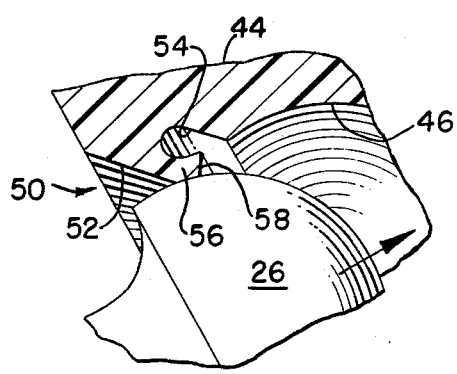
FIG. 2A is an enlarged fragmented view similar to FIG. 2 illustrating insertion of one of the components into another component during an assembly procedure.
Figure 3:
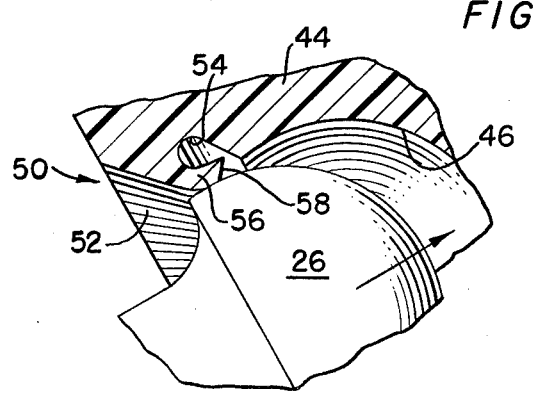
FIG. 3 is another enlarged fragmented view similar to FIG. 2A, illustrating a different position of the components of the prosthesis during the assembly procedure.

As the head 26 is forced inwardly relative to cavity 46, lip member 56 is deformed inwardly, as depicted in FIGS. 2, 2A, and 3, to partially collapse groove 54. The deflection of lip member 56 may continue until the diameter of the opening 48 is at least equal to the diameter of head member 26. Accordingly, the femur head member 26 may pass into cavity 46 and assume the assembled condition such as shown in FIG. 4. By reason of its inherent resiliency, lip member 56 then resumes the undeformed condition as indicated by the solid lines in FIG. 4 and the opening 48 assumes its normal diameter. In the assembled condition, the head member 26 will remain entrapped within cavity 46 by virtue of the fact that the diameter of undeformed opening 48 is less than the diameter of spherical head member 26. It is possible to withdraw the head member 26 from the cavity if sufficient force is applied. However, deformable lip member 56 normally serves to even more tightly entrap the head member 26 within the cavity 46 and resist forces which would withdraw the head member from the cavity 46, since if such a force is applied by the head member 26 to the lip member 56, it will force the latter outwardly with respect to the cavity 46, the lip member will bend outwardly as illustrated in FIG. 6 and, as a result, the diameter of the opening 48 correspondingly decreases to a dimension which is less than the normal first diameter of such opening as defined by the undeformed lip member 52. It will be appreciated, therefore, that an arrangement is provided to even more positively and tightly entrap the head member 26 within cavity 46 against any tendency for separation or dislocation of the assembled joint.

While the foregoing description has described the preferred embodiment as having the groove continuously annular and angularly oriented so as to be parallel to the guideway, other embodiments are envisioned wherein the groove need not be entirely annular and angularly oriented in such a fashion that it is concentric to the spherical cavity or parallel to the guideway, without departing from the spirit and scope of this invention. The other embodiments which might be so formed should be arranged such that the lip member is deformable and capable of resilient return to a position whereby it entraps the head member within the cavity formed in the prosthesis member. Accordingly, a non-dislocatable coupled hip joint prosthesis is formed which facilitates that normal type movement between femur and acetabulum socket.

The foregoing described artificial anatomical joint has been directed to the hip joint. The broader aspects of this invention envision its utilization in other anatomical joints such as, for example, the shoulder joint. Specifically referring to FIG. 7, a shoulder joint type prosthesis 60 is disclosed, including an implantable insert member 62 having a substantial spherical head 64 with smooth and low-friction characteristics, and a stem 66 adapted to be inserted to the appropriate anatomical shoulder structure. A shield or casing member 68 is provided having an elongated stem 70 with a plurality of serrated projections 72 designed to secure the casing 68 to a corresponding anatomical structure. The casing 68 is also formed with a hollow portion which securely receives prosthesis insert means 74. The prosthesis insert means 74 is similar to prosthesis means 14. Such prosthesis means 74 includes guideway 76, groove 78 and lip member 80. The materials forming the above described shoulder prosthesis may be similar to that of the previously described embodiment. Alternatively, the casing member 68 may be made from Ultra High Molecular Weight Polyethylene. A further embodiment is one in which casing member 68 and prosthesis insert means 74 are made as a single unit from U.H.M.W.P. Other suitable materials consistent with this invention may be provided.

While the invention has been described in connection with preferred embodiments, it is not intended to limit the invention to the particular forms set forth above. It is intended to cover alternatives, modifications, and equivalents included within the spirit and scope of the invention as defined by the appended claims.

What is claimed is:

1. An articulating joint prosthesis comprising implantable first and second members, said first member having a substantially spherical head, said second member having a substantially congruent cavity formed therein for cooperatively engaging said spherical head, said cavity having a hemispherical portion terminating in a diametral plane and an entrance portion extending beyond said plane and terminating in a circular entrance to said cavity, and outwardly tapering guideway surrounding said entrance, said second member further having a continuous annular groove formed substantially at said diametral plane and adjacent said guideway, said guideway and said groove defining between them a resilient annular lip surrounding said entrance, said lip being inwardly deformable during insertion of said spherical head through said entrance to admit and entrap said head in said cavity, and said lip being outwardly deformable to resist escape of said head from said cavity.

2. A hip joint prosthesis comprising the prosthesis of claim 1 wherein said first member is provided with means for implanting in the femur and said second member has a substantially spherical outer surface for implanting in the acetabulum.

3. The prosthesis of claim 2 wherein said second component is formed from a resilient low friction polymer encased in a metallic outer shell.

4. The prosthesis of claim 3 wherein said polymer is ultrahigh molecular weight polyethylene and said shell has a generally smooth, unbroken and spherical conformation.

5. An implantable component for cooperatively engaging an implantable prosthetic member having a substantially spherical head to form an articulating joint prosthesis, said component having a substantially congruent cavity formed therein for cooperatively engaging said spherical head, said cavity having hemispherical portion terminating in a diametral plane and an entrance portion extending beyond said plane and terminating in a circular entrance to said cavity, an outwardly tapering guideway surrounding said entrance, said component further having a continuous annular groove formed substantially at said diametral plane and adjacent said guideway, said guideway and said groove defining between them a resilient annular lip surrounding said entrance, said lip being inwardly deformable during insertion of said spherical head through said entrance to admit and entrap said head in said cavity, and said lip being outwardly deformable to resist escape of said head from said cavity.

6. The component of claim 5 wherein the walls of said annular groove are substantially parallel to the wall of said tapered guideway.

7. The component of claim 5 formed from a resilient low friction polymer.

8. The component of claim 7 wherein said polymer is ultrahigh molecular weight polyethylene and said component is encased in a metallic outer shell.

9. The component of claim 8 wherein said shell has a generally smooth, unbroken and spherical conformation.

* * * * *

UNITED STATES PATENT AND TRADEMARK OFFICE
CERTIFICATE OF CORRECTION

PATENT NO. : 4,044,403
DATED : August 30, 1977
INVENTOR(S) : Joseph D'Errico

It is certified that error appears in the above-identified patent and that said Letters Patent are hereby corrected as shown below:

1. In the Abstract, lines 3-4, "having substantially congruent" should read --having a substantially congruent--.

2. In column 1, line 22, "Convention" should read --Conventional--.

3. In column 3, line 48, "illustrating" should read --illustration--.

Signed and Sealed this

Twenty-ninth Day of November 1977

[SEAL]

Attest:

RUTH C. MASON
*Attesting Officer*

LUTRELLE F. PARKER
*Acting Commissioner of Patents and Trademarks*